United States Patent
Sekine et al.

(10) Patent No.: US 7,786,296 B2
(45) Date of Patent: Aug. 31, 2010

(54) SILYL LINKER FOR SOLID-PHASE SYNTHESIS OF NUCLEIC ACID

(75) Inventors: Mitsuo Sekine, Yokohama (JP); Kohji Seio, Yokohama (JP); Akihiro Ohkubo, Machida (JP)

(73) Assignee: Japan Science and Technology Agency, Kawaguchi-shi Saitama (JP)

( * ) Notice: Subject to any disclaimer, the term of this patent is extended or adjusted under 35 U.S.C. 154(b) by 697 days.

(21) Appl. No.: 10/590,267

(22) PCT Filed: Feb. 10, 2005

(86) PCT No.: PCT/JP2005/002059

§ 371 (c)(1),
(2), (4) Date: Jul. 2, 2007

(87) PCT Pub. No.: WO2005/080404

PCT Pub. Date: Sep. 1, 2005

(65) Prior Publication Data

US 2008/0051571 A1    Feb. 28, 2008

(30) Foreign Application Priority Data

Feb. 25, 2004    (JP) .............................. 2004-049303

(51) Int. Cl.
*C07H 19/00* (2006.01)
*C07H 19/048* (2006.01)

(52) U.S. Cl. ............... 536/28.1; 536/22.1; 536/23.1; 536/25.3; 536/26.1; 536/26.8

(58) Field of Classification Search ............ None
See application file for complete search history.

(56) References Cited

U.S. PATENT DOCUMENTS

| | | | |
|---|---|---|---|
| 3,831,173 A | 8/1974 | Lerner | |
| 5,512,834 A | 4/1996 | McEwan | |
| 5,576,624 A | 11/1996 | Candy | |
| 6,362,737 B1 | 3/2002 | Rodgers et al. | |
| 6,586,938 B1 | 7/2003 | Paltoglou | |
| 6,617,856 B1 | 9/2003 | Royle et al. | |
| 6,617,864 B2 | 9/2003 | Inoue et al. | |
| 6,954,072 B1 | 10/2005 | Schlapp et al. | |
| 6,977,504 B2 | 12/2005 | Wright et al. | |
| 2002/0030492 A1 | 3/2002 | Guo et al. | |
| 2005/0104595 A1 | 5/2005 | Nelson | |
| 2005/0159929 A1 | 7/2005 | Overby et al. | |
| 2005/0253721 A1 | 11/2005 | Herring et al. | |

FOREIGN PATENT DOCUMENTS

GB    2 247 381 A    2/1992

OTHER PUBLICATIONS

Office action dated Feb. 17, 2006, received in U.S. Appl. No. 10/759,747.
Amendment and Response to Office action dated Jul. 17, 2006, filed in U.S. Appl. No. 10/759,747.
Akio Kobori et al.; A new silyl ether-type linker useful for the automated synthesis of oligonucleotides having base-labile protective groups; Chemistry Letters, 2002, No. 1, pp. 16-17.
Marie Florence Grenier-Loustalot et al.; Mechanisms and kinetics of polymerization of thermoplastic polyimides. II. Study of bridged dianhydride/aromatic amine systems, Journal of Polymer Science, Part A: Polymer Chemistry, 1993, vol. 31, No. 12, pp. 3049-3063.

*Primary Examiner*—Patrick T Lewis
(74) *Attorney, Agent, or Firm*—Birch, Stewart, Kolasch & Birch, LLP.

(57) ABSTRACT

The purpose of the invention is to develop a silyl linker that can be efficiently introduced on a solid-phase support used for the synthesis of nucleic acid oligomers such as DNA. The present invention relates to a silyl linker for use in the solid-phase synthesis of nucleic acid, comprised of a compound of the general formula or its ester or salt:

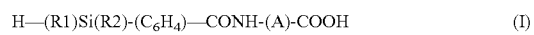

H—(R1)Si(R2)-(C$_6$H$_4$)—CONH-(A)-COOH    (I)

wherein each of R1 and R2 is an alkyl or aryl group, and (A) represents a spacer moiety; a 3'-end nucleoside unit having said compound linked via an oxygen atom to the 3-position of a sugar of the nucleoside or its derivative, a solid-phase support having the 3'-end nucleoside unit, and a method for synthesis of nucleic acid oligomer with the use of said solid-phase support.

10 Claims, 1 Drawing Sheet

```
                            SEQUENCE LISTING

<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: A DNA oligomer chemically synthesized using the
      silyl linker

<400> SEQUENCE: 1
gcatcagcct cat                                                          13
```

SILYL LINKER FOR SOLID-PHASE SYNTHESIS OF NUCLEIC ACID

FIELD OF THE INVENTION

The invention relates to a silyl linker that can be efficiently introduced on a solid-phase support used for the synthesis of nucleic acid (DNA).

BACKGROUND ART

In the progress of diversification of the studies relating to nucleic acids, it is desired to rapidly synthesize with a high purity a functional molecule such as a DNA oligomer liable to oxidative deterioration or a DNA oligomer having a functional moiety unstable under a basic condition, which would be decomposed in such a basic condition as is usually used in DNA synthesis (the treatment with ammonia).

Up to now, a benzoic acid-type compound: $iP_2Si—C_6H_4—C(O)—$ type that was developed by one of the present inventors, SEKINE Mitsuo, is known as a silyl linker that can be cut out under a neutral condition (Non-Patent Document 1). However, it was not practically sufficient since it would take such a long time as almost one day to introduce the above compound on a solid-phase support, and an introduction efficiency is as low as 6-8 μmol/g, especially on HCP solid phase having a small amount of the total amino groups (34 μmol/g).

Non-Patent Document 1: Kobori, A.; Miyata, K.; Ushioda, M.; Seio, K.; Sekine, M., Chemistry Letters, 2002, 16-17.

SUMMARY OF THE INVENTION

Problems to be Solved by the Invention

The purpose of the present invention is therefore to develop a silyl linker that can be efficiently introduced on the solid-phase support. The present inventors have studied hard so that the above purpose was accomplished by introducing a spacer into the conventional silyl linker, leading to the present invention.

Thus, the present invention relates to a silyl linker for use in the solid-phase synthesis of nucleic acid, comprised of a compound of the general formula or its ester or salt:

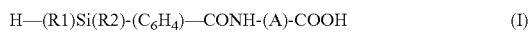

$$H—(R1)Si(R2)-(C_6H_4)—CONH-(A)-COOH \quad (I)$$

wherein each of R1 and R2 is an alkyl or aryl group, and (A) represent a spacer moiety.

The present invention further relates to a 3'-end nucleoside unit having the above compound linked via an oxygen atom to the 3-position of a sugar of the nucleoside or its derivative wherein, for example, a hydroxy group at 5-position of the sugar is protected with an appropriate protecting group. The above unit will be especially advantageous when a thymine group is constituting the nucleoside because the thymine has no amino group to be protected in the introduction on the solid-phase.

The present invention also relates to a solid-phase support, especially HCP solid-phase support having the above 3'-end nucleoside unit or the above silyl linker for use in the solid-phase synthesis of nucleic acid. The solid-phase support itself is known for those skilled in the art. The present invention also relates to a method for synthesis of a nucleic acid oligomer with the use of the solid-phase support according the present invention. This method is advantageous, especially for the synthesis of a nucleic acid oligomer containing modified bases that are unstable under a basic condition, such as an acetylated cytosine.

Advantages of the Invention

The silyl linker according to the present invention may be cut out under a neutral condition, and will significantly increase the introduction ratio of the 3'-end nucleoside unit on the solid-phase support up to about 20-30 μmol/g that is thought to be most suitable in the DNA synthesis.

BEST MODE FOR CARRYING OUT THE INVENTION

Figure 1:
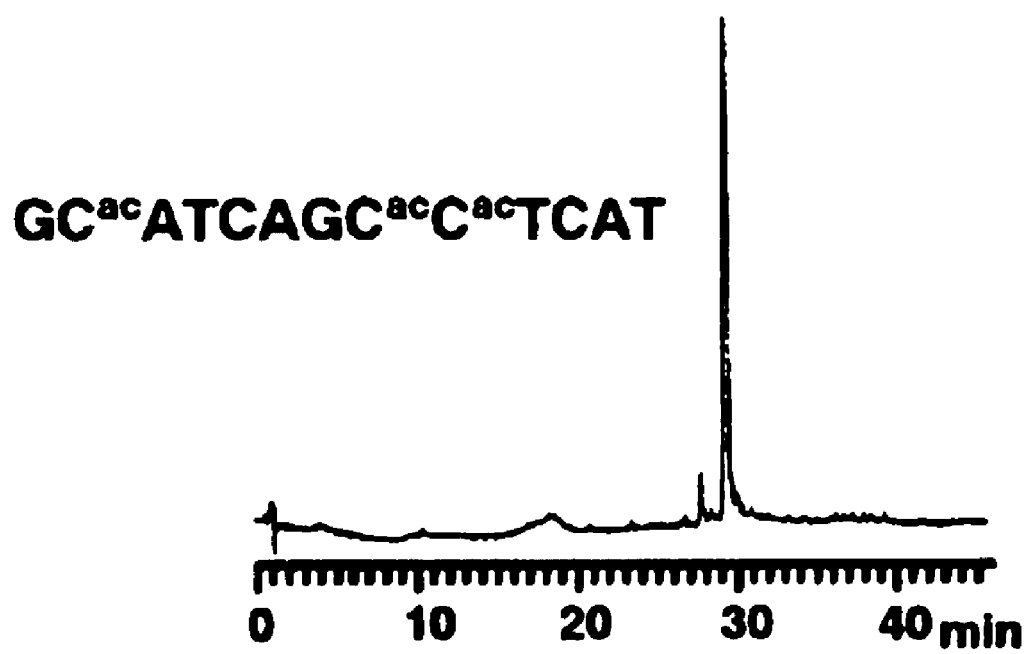
FIG. 1 shows a chart in a reverse and anion-exchange chromatography of d[GC$^{ac}$ATCAGC$^{ac}$C$^{ac}$TCAT] (SEQ ID NO: 1) synthesized with the use of the silyl linker.

Any moiety known for those skilled in the art may be used as the spacer moiety (A) as long as it can accomplish a desired purpose of the present invention. For example, an alkylene group represented by the formula: $—(CH_2)n-$ (II) wherein "n" is a natural number, preferably 2-18 may be used as the spacer. The alkylene group may have at least one other group such as ether or thioether bond.

The silyl group may have any substituents of R1 and R2 known for those skilled in the art, such as, for example, an alkyl group having 1 to 5 carbon atoms or an aryl group such as benzyl, phenyl and naphthyl group, which may have a substituent of the above alkyl, nitro, cyano, halogeno or alkoxy group at any position.

Furthermore, the benzene ring structure of the present compound may have any substituent known for those skilled in the art, which, for example, is selected from the group consisting of alkyl having 1 to 4 carbon atoms, halogeno, nitro, cyano and methoxy groups. The groups of "—CONH—" and "Si" are bound to the benzene ring in a para-position.

The ester or salt according to the present invention may be optionally selected from any compounds known for those skilled in the art, which includes triethyl ammonium salt, tributyl ammonium salt and ethyldiisopropyl ammonium salt; and cyanoethylester, allylester and 4-nitrophenylethyl ester.

The compound of the present invention may be easily synthesized by those skilled in the art with reference to the following examples. Conditions that are not specifically described in the present specification may be optionally selected by those skilled in the art.

EXAMPLES

The present invention will be explained more in detail in line with the examples, which should not be construed to impose any limitations on the scope of the present invention.

Example 1

Synthesis of Silyl Linker 4-diisopropylsilanylbenzoyl chloride (2)

4-diisopropylsilanyl benzoic acid (1) (6.7 g, 28.4 mmol) and thionyl chloride (3.2 mL, 42.6 mmol) were mixed together and heated to reflux for 2 hours. a desired compound was then purified and identified by distillation under a reduced pressure (1 mmHg, 102-104° C.) (5.6 g, 77%). Its NMR data are as follows:

$^1$H NMR (CDCl$_3$): 0.95-1.06 (m, 12H), 1.21-1.29 (m, 2H), 3.99 (t, 1H, J=3.1 Hz), 7.64 (d, 2H, J=7.8 Hz), 8.03 (d, 2H, J=7.8 Hz).

$^{13}$C NMR (CDCl$_3$): 10.7, 18.5, 18.7, 130.0, 133.6, 135.9, 144.5, 168.3.

4-[4-(diisopropylsilanyl)benzoylamino]butanoic acid (3)

4-diisopropylsilanylbenzoyl chloride (2) (1.7 g, 6.7 mmol) was added into 1N sodium hydroxide aqueous solution (9 mL) dissolving 4-aminobutanoic acid (910 mg. 8.94 mmol) and stirred for 8 hours. After the addition of 12N hydrochloric acid to the aqueous solution to reach pH 2, the solution was extracted with 400 mL of CH$_2$Cl$_2$ and an organic layer was then collected. The resulting organic layer was dehydrated with anhydrous sodium sulfate and filtered so that the resulting solvent was distilled out under a reduced pressure. A desired compound was then purified by silica gel column chromatography. After eluted with chloroform having 0-3% methanol gradient, the solvent was distilled out to give the desired compound as white solid (1.4 g, 65%). Its NMR data are as follows:

$^1$H NMR (CDCl$_3$): 0.93-1.06 (m, 12H), 1.16-1.25 (m, 2H), 1.94 (t, 2H, J=4.1 Hz), 2.45 (t, 2H, J=6.9 Hz), 3.50 (dd, 2H, J=6.5 Hz, J=9.7 Hz), 3.93 (t, 1H, J=3.1 Hz), 6.77 (brs, 1H), 7.54 (d, 2H, J=8.1 Hz), 7.72 (d, 2H, J=8.1 Hz).

$^{13}$C NMR (CDCl$_3$): 10.5, 17.9, 18.3, 18.4, 24.3, 31.6, 39.5, 57.9, 77.2, 125.8, 134.3, 135.3, 138.6, 168.3, 176.6.

4-[4-(diisopropylsilanyl)benzoylamino]butanoic acid 2-cyanoethyl ester (4)

A condensing agent of N,N-bis (2-oxo-3-oxazolidinyl)-phosphnic acid chloride BOP-Cl (1.5 g, 6.1 mmol) was added to pyridine solution (20 mL) dissolving 4-[4-(diisopropylsilanyl)benzoylamino]butanoic acid (3) (1.3 g, 4.1 mmol), 2-cyanoethanol (548 μL, 8.1 mmol) and triethylamine (828 μL, 6.1 mmol). The resulting mixture was stirred for 3 hours at a room temperature and mixed with water (5 mL). Five minutes later, it was diluted with chloroform (200 mL) and extracted three times with 5 wt % aqueous solution (150 ml) of sodium hydrogen carbonate. An organic layer was collected and dehydrated with anhydrous sodium sulfate and filtered so that the resulting solvent was distilled out under a reduced pressure. The resulting crude product was then purified by silica gel column chromatography. After eluted with chloroform having 0-3% methanol gradient, the solvent was distilled out to give a desired product (1.2 g, 79%). Its NMR data are as follows:

$^1$H NMR (CDCl$_3$): 0.89-1.00 (m, 12H), 1.15-1.21 (m, 2H), 1.89 (t, 2H, J=6.9 Hz), 2.40 (t, 2H, J=7.0 Hz), 2.62 (t, 2H, J=6.2 Hz), 3.42 (dd, 2H, J=6.6 Hz, J=12.8 Hz), 3.89 (t, 1H, J=3.0 Hz), 4.18 (t, 2H, J=6.2 Hz), 6.99 (brs, 1H), 7.49 (d, 2H, J=7.6 Hz), 7.72 (d, 2H, J=7.8 Hz).

$^{13}$C NMR (CDCl$_3$): 10.4, 17.8, 18.3, 18.4, 24.4, 31.2, 39.1, 58.5, 77.2, 116.7, 125.7, 134.7, 135.3, 138.4, 167.4, 172.4.

5'-O-(4,4'-dimethoxytrityl)-thymidine-3'-O-diisopropylsilyl-4-benzoylaminobutanoic acid triethylammonium (6)

4-[4-(diisopropylsilanyl)benzoylamino]butanoic acid 2-cyanoethyl ester (4) (1.1 g, 2.9 mmol) was dissolved into anhydrous CH$_2$Cl$_2$ (15 mL) and to this solution was added 1,3-dichloro-4,4-dimethylhydantoin (1.2 g, 5.9 mmol). The resulting mixture was stirred for 30 min at a room temperature and mixed into anhydrous CH$_2$Cl$_2$ (10 mL) dissolving 5'-O-(4,4'-dimethoxytrityl)-thymidine (3.2 g, 5.9 mmol) and imidazole (2.0 g, 29.4 mmol). The resulting mixture was stirred for 30 min at a room temperature and mixed with water (5 mL). Five minutes later, it was diluted with chloroform (100 mL) and extracted three times with a 5 wt % aqueous solution (150 ml) of sodium hydrogen carbonate. An organic layer was collected and dehydrated with anhydrous sodium sulfate and filtered so that the resulting solvent was distilled out under a reduced pressure. The resulting crude product was then purified by silica gel column chromatography (1% pyridine). After eluted with hexane having 30-100% chloroform gradient, the solvent was distilled out. The residue was then dissolved in acetonitrile (30 mL), mixed with DBU (1.7 mL, 11.2 mmol) and stirred for 30 min at a room temperature. The resulting mixture was then mixed with 0.5 M triethyl ammonium carbonate buffer (100 mL) and subjected to extraction with chloroform (100 mL). An organic layer was collected and dehydrated with anhydrous sodium sulfate and filtered so that the resulting solvent was distilled out under a reduced pressure. The resulting crude product was then purified by silica gel column chromatography. After eluted with chloroform comprising 1% triethylamine having 0-3% methanol gradient, the solvent was distilled out to give a desired product (1.5 g, 54%). Its NMR data are as follows:

$^1$H NMR (CDCl$_3$): 0.92-1.08 (m, 12H), 1.18-1.30 (m, 11H), 1.49 (s, 3H), 1.93 (t, 2H, J=6.3 Hz), 2.35-2.47 (m, 4H), 3.42 (d, 2H, J=7.3 Hz), 3.45-3.75 (m, 8H), 3.78 (s, 6H), 4.14 (s, 1H), 4.64 (s, 1H), 6.44 (t, 1H, J=6.8 Hz), 6.80 (d, 4H, J=7.6 Hz), 7.18-7.80 (m, 14H).

Example 2

Preparation of Solid-Phase Support (7)

Sufficiently dried solid-phase support (highly cross-linked polystyrene: HCP) (500 mg. 52 μmol), 5'-O-(4,4'-dimethoxytrityl)-thymidine-3'-O-diisopropylsilyl-4-benzoylaminobutanoic acid triethylammonium (6) (260 μmol) and DCC (268 mg, 1.3 mmol) were dissolved into dichloromethane (5 mL) and stirred for 12 hours at a room temperature. After the completion of the reaction, the solid-phase support was filtered, washed with acetonitrile, dried and added to solution made of pyridine (4.5 mL), anhydrous acetic acid (0.5 ml) and DMAP (5 mg). After being stirred for 3 hours, the solid-phase support was filtered again and washed with acetonitrile. The introduction ratio of the compound was measured by colorimetric determination of the trityl group (21 μmol/g). The above synthesis steps were shown in the following chemical formulae 1 and 2.

[Chemical formula 1]
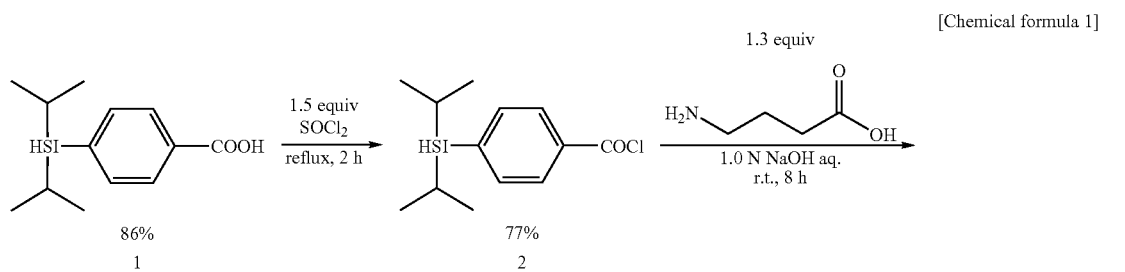
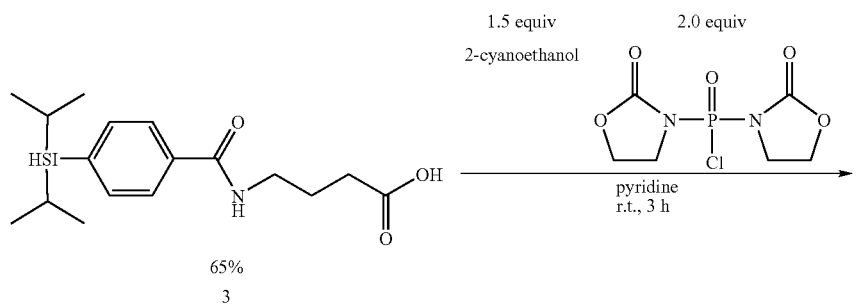
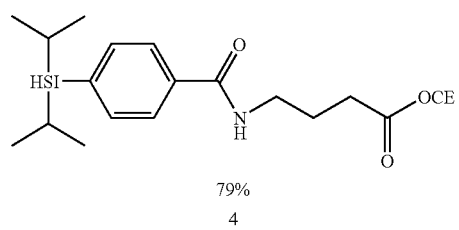
[Chemical formula 2]
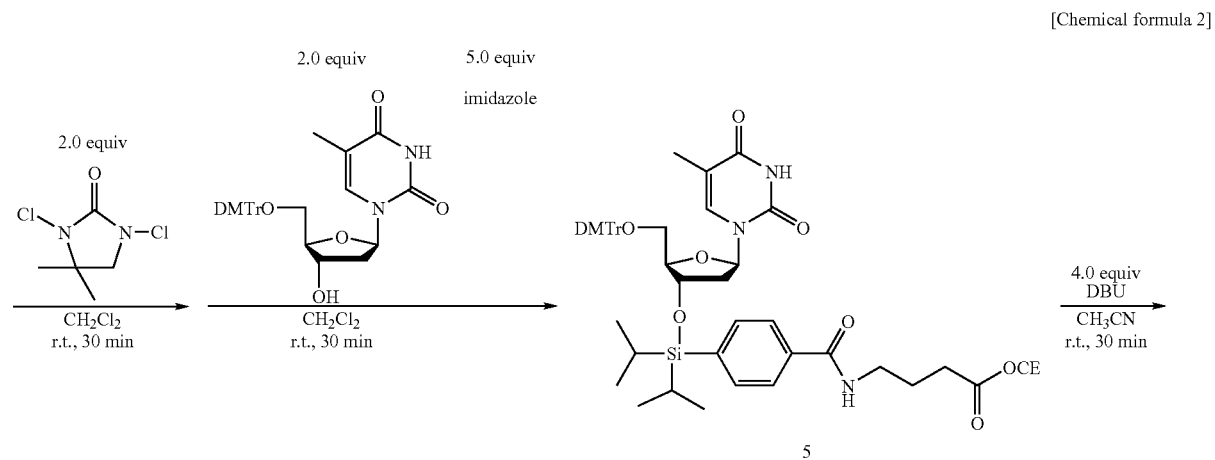

-continued

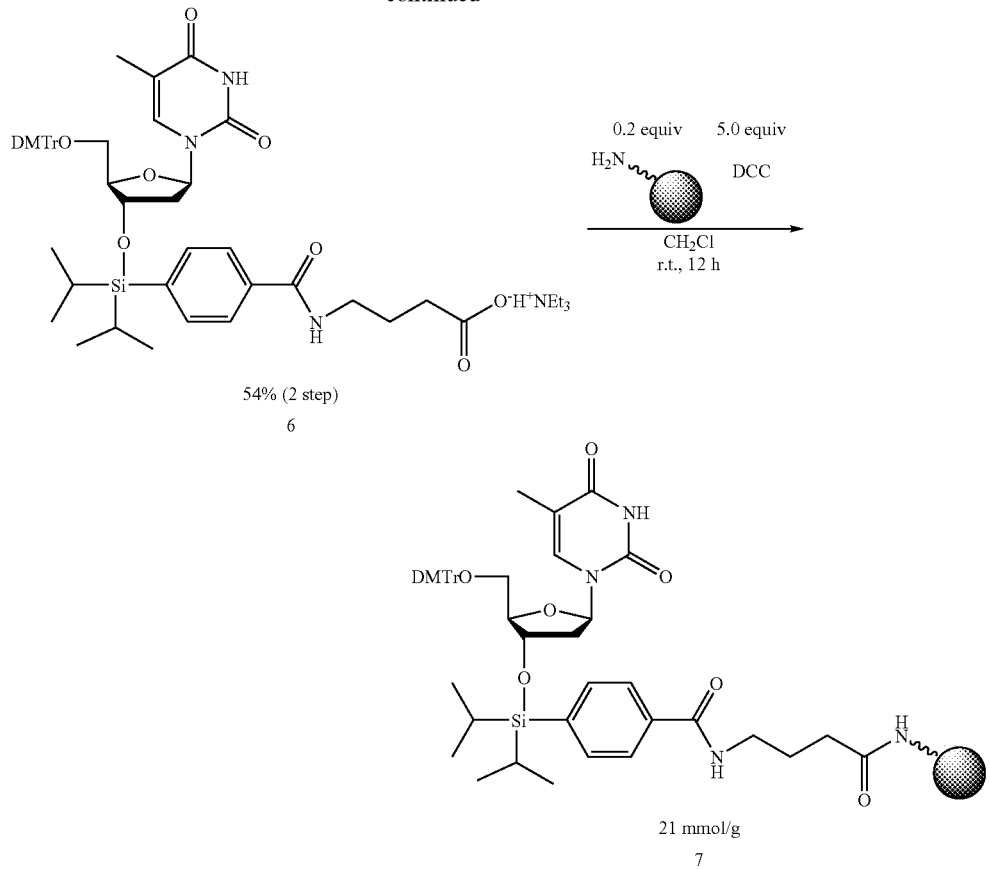

54% (2 step)
6

21 mmol/g
7

Example 3

DNA Synthesis with the Use of the Silyl Linker

A DNA 13-mer: d[GC$^{ac}$ATCAGC$^{ac}$C$^{ac}$TCAT] (SEQ ID NO: 1) wherein the amino groups in some of the cytosine bases were acetylated was synthesized. Such acetyl group was unstable under such a weakly basic condition as ammonia. However, the acetylated cytosine base will form a base pair of Watson-Crick type with a guanine base and a DNA oligomer comprising such acetylated cytosine base will therefore have a specialized property such as a higher forming capacity of a double strand than that comprising a natural cytosine base.

The DNA oligomer was automatically synthesized with the use of the HCP solid-phase support (7) (1 µmol, 21 µmol/g) by means of DNA/RNA Synthesizer 392 (Applied Biosystem Inc.: ABI). Each elongation cycle of the oligomer was shown in TABLE 1 below.

TABLE 1

| Step | operation | Reagent(s) | time, (min) |
|---|---|---|---|
| 1 | washing | CH$_3$CN | 0.2 |
| 2 | detritylation | 3% Cl$_3$CCOOH/CH$_2$Cl$_2$ | 1.5 |
| 3 | washing | CH$_3$CN | 0.4 |
| 4 | coupling | 0.1M amidite + 0.2M HO$^d$Bt in CH$_3$CN-NMP (15:1, v/v) | 1.0 |
| 5 | washing | CH$_3$CN | 0.2 |
| 6 | coupling | 0.1M amidite + 0.2M HO$^d$Bt in CH$_3$CN-NMP (15:1, v/v) | 1.0 |

TABLE 1-continued

| Step | operation | Reagent(s) | time, (min) |
|---|---|---|---|
| 7 | washing | CH$_3$CN | 0.2 |
| 8 | oxidation | 0.1M I$_2$ in Py-H$_2$O-THF (20:2:78, v/v/v) | 0.5 |
| 9 | washing | CH$_3$CN | 0.4 |

The DMTr group was then removed by the treatment with 3% trichloroacetic acid in CH$_2$Cl$_2$ (2 mL) for one minute, and the solid-phase support was washed with CH$_2$Cl$_2$ (1 mL×3) and CH$_3$CN (1 mL×3). The cyanoethyl group was then removed by the treatment with 10% DBU in CH$_3$CN (500 µL). After being washed with CH$_3$CN (1 mL×3), the solid-phase support was treated with anhydrous THF solution (500 µL) dissolving TBAF (131 mg, 0.5 mmol) and acetic acid (24 µL, 0.5 mmol) for one hour in order to cut out the DNA oligomer. The resulting mixture solution was desalted with Sep-Pak C18 cartridge, diluted with water and subjected to reverse and anion-exchange HPLC for analysis. The results by mass spectrometry of the resulting compound are as follows: d[GC$^{ac}$ATCAGC$^{ac}$C$^{ac}$TCAT] (SEQ ID NO: 1) Mass (M-H) calcd. 4017.72. found 4018.00.

INDUSTRIAL APPLICABILITY

It will be easy to synthesize DNA derivatives comprising various functional groups that are unstable under the basic condition by using the silyl linker or the 3'-end nucleoside unit according to the present invention.

What is claimed is:

1. A silyl linker for use in the solid-phase synthesis of nucleic acid, comprised of a compound of the general formula or its ester or salt:

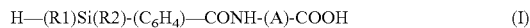  (I)

wherein the benzene ring structure is optionally further substituted, each of R1 and R2 is an alkyl, and (A) is an alkylene group represented by the formula —$(CH_2)_n$— wherein n is 2-18.

2. The compound according to claim 1 wherein R1 and R2 are an alkyl group having 1 to 5 carbon atoms.

3. The compound according to claim 1 wherein the benzene ring structure (—$(C_6H_4)$—) has a substituent.

4. The compound according to claim 3 wherein the substituent of the benzene ring structure is selected from the group consisting of alkyl having 1 to 4 carbon atoms, halogeno, nitro, cyano and methoxy groups.

5. A 3'-end nucleoside unit having the compound according to claim 1 linked via an oxygen atom to the 3-position of a sugar of a nucleoside or its derivative.

6. The 3'-end nucleoside unit according to claim 5 wherein a base constituting the nucleoside is thymine.

7. The compound according to claim 6 which is 5'-O-(4,4'-dimethoxytrityl)-thymidine-3'-O-diisopropylsilyl-4-benzoylaminobutanoic acid triethylammonium.

8. A solid-phase support having the 3'-end nucleoside unit according to claim 5 introduced thereon.

9. The solid-phase support according to claim 8 having the 3'-end nucleoside unit at a ratio of 20-30 μmol/g.

10. The solid-phase support according to claim 8 or 9, which is a highly cross-linked polystyrene (HCP) solid-phase support.

* * * * *